United States Patent [19]

Sie et al.

[11] Patent Number: 4,868,221

[45] Date of Patent: Sep. 19, 1989

[54] PROCESS FOR THE PRODUCTION OF METHANOL AND A COMPOSITION SUITABLE FOR USE AS A CATALYST IN SAID PROCESS

[75] Inventors: Swan T. Sie; Eit Drent; Willem W. Jager, all of Amsterdam, Netherlands

[73] Assignee: Shell Oil Company, Houston, Tex.

[21] Appl. No.: 175,027

[22] Filed: Mar. 30, 1988

[30] Foreign Application Priority Data

Apr. 3, 1987 [GB] United Kingdom ................. 8708004

[51] Int. Cl.$^4$ ....................... C07C 27/06; C07C 31/04
[52] U.S. Cl. .................................... 518/700; 518/717; 502/170
[58] Field of Search ........................ 518/700, 715, 717

[56] References Cited

U.S. PATENT DOCUMENTS 4,614,749 9/1986 Sapienza et al. ..................... 518/700
4,619,946 10/1986 Sapienza et al. ..................... 518/700

FOREIGN PATENT DOCUMENTS 56169634 12/1981 Japan .

Primary Examiner—Howard T. Mars
Attorney, Agent, or Firm—Y. Grace Tsang

[57] ABSTRACT

A process for the preparation of methanol by contacting CO and $H_2$ with a novel catalytic system formed by combining (a) a nickel salt having a $pK_a < 4.70$, (b) an alcohol, and (c) a hydride of an alkali metal or of an alkaline earth metal.

12 Claims, No Drawings

PROCESS FOR THE PRODUCTION OF METHANOL AND A COMPOSITION SUITABLE FOR USE AS A CATALYST IN SAID PROCESS

FIELD OF THE INVENTION

The invention relates to a process for the production of methanol. The invention also relates to a novel catalyst composition.

BACKGROUND OF THE INVENTION

A process for the production of methanol is described in U.S. patent specification No. 4,619,946, issued Oct. 28, 1986, which concerns reacting carbon monoxide with hydrogen in the presence of a catalytic system of the type NaH—RONa— nickel acetate in which R represents an alkyl group having 1–6 carbon atoms. This catalytic system can be made more active by "conditioning," involving contacting for a prolonged time with a gaseous mixture comprising carbon monoxide and hydrogen at such an elevated temperature and elevated pressure that a substantial amount of carbon monoxide and hydrogen is consumed for this "conditioning."

Another process for the production of methanol is described in Japanese patent application publication No. 56-169,634, published Dec. 26, 1981, which concerns reacting carbon monoxide and hydrogen in the presence of a catalyst comprising a nickel compound and an alkali metal alkoxide.

It is an object of the present invention to produce methanol in the presence of a catalytic system having enhanced activity.

It is another object of the present invention to produce methanol in the presence of a catalytic system that retains its activity for a long time.

SUMMARY OF THE INVENTION

The invention provides a process for the production of methanol which process comprises contacting a gaseous mixture comprising carbon monoxide and hydrogen with a catalytic system prepared by combining the following components:

component (a): a nickel salt of an acid having a $pK_a$, measured in aqueous solution at 25° C., of less than 4.70,
component (b): an alcohol, and
component (c): a hydride of an alkali metal and/or a hydride of an alkaline earth metal.

DETAILED DESCRIPTION OF THE INVENTION

The anion of the salt in component (a) may be derived from a great variety of acids having a pKa, measured in aqueous solution at 25° C., of less than 4.70. It is preferred that the salt in component (a) is a salt of a carboxylic acid. Among these acids preference is given to formic acid and oxalic acid. Component (a) is most preferably nickel formate or nickel oxalate.

Examples of carboxylic acids from which component (a) may be derived are dicarboxylic acids such as malonic acid, dimethylmalonic acid, succinic acid, glutaric acid, adipic acid, pimelic acid, suberic acid, azelaic acid, phthalic acid, isophthalic acid and terephthalic acid. The carboxylic acids from which component (a) may be derived may contain substituents, for example, alkoxy groups, particularly those having not more than five carbon atoms, hydroxy groups, cyano groups and fluorine, chloride, bromine and iodine atoms. Examples of such carboxylic acids are glycolic acid, 2-hydroxypropionic acid, 3-hydroxypropionic acid, glyceric acid, tartronic acid, malic acid, tartaric acid, tropic acid, benzilic acid, salicylic acid, anisic acid, gallic acid, 3,5-dichlorobenzoic acid, 3,5-dibromobenzoic acid, cyanoacetic acid, monofluoroacetic acid, difluoroacetic acid, trifluoroacetic acid and trichloroacetic acid. Component (a) is not derived from acetic acid, having $pK_a$ of 4.75, as the only acid. It is, however, not excluded from the scope of the present invention that component (a) contains anions of a carboxylic acid having a $pK_a$ of less than 4.70 and also anions of acetic acid.

A mixture of the above-mentioned salts may be used in component (a). For example, a mixture of a formate and an oxalate or a mixture of a formate and a benzoate can be used.

The salts in component (a) may contain crystal water, but are preferably free therefrom.

The alcohol of component (b) may be aromatic or cycloaliphatic but is preferably aliphatic. Preference is given to alkanols, in particular to those having in the range of from 1 to 20 carbon atoms per molecule. Among the latter alknaols those having in the range of from 4 to 12 carbon atoms per molecule are preferred, because such alkanols can be easily separated from methanol by means of distillation. Examples of such alkanols are tert-butyl alcohol, tert-pentyl alcohol, hexanol, heptanol and alkanols having in the range of from 8 to 12 carbon atoms per molecule. Tert-butyl alcohol and tert-pentyl alcohol are particularly preferred. Dihydric alcohols may also be used, for example, ethylene glycol, propylene glycol, 1,3-dihydroxypropane, 1,2-butanediol, 1,3-butanediol, 1,4-butanediol, 2,3-butanediol or 1,2-pentanediol. Component (b) may also be glycerol.

Component (b) may be a mixture of alcohols, for example, of tert-butyl alcohol and ethylene glycol or of tert-pentyl alcohol and 1,4-butanediol.

Component (c) may be a hydride of lithium, sodium, potassium, rubidium, cesium, calcium, strontium, barium or magnesium. Preference is given to sodium hydride. The hydride may be added as such, but it has been found that the hydride may advantageously be added as a suspension in an inert diluent, for example, a mineral oil, such as a heavy hydrocarbon oil, preferably a so-called white paraffin oil.

If desired, an alcoholate of an alkali metal or an alcoholate of an alkaline earth metal may also be combined in the catalytic system. This alcoholate is preferably a sodium alcoholate or a potassium alcoholate. Among the alcoholates preference is given to alkoxides, particularly to those having in the range of from 1 to 20 carbon atoms per molecule, such as sodium methoxide, sodium ethoxide, sodium propoxides, sodium butoxide, sodium isobutoxide, sodium tert-pentoxide and potassium 2-methyldodec-2-oxide.

It has, furthermore, been found that the activity of the catalytic system can be further enhanced by a pretreatment. According to a preferred embodiment of the present invention the catalytic system is pre-treated by contacting it for a prolonged time with a gaseous mixture comprising carbon monoxide and hydrogen at such an elevated temperature and elevated pressure that no substantial consumption of carbon monoxide and hydrogen takes place during the pre-treatment. Usually, a period in the range of from 10 minutes to 5 hours at a temperature between 30° C. and 150° C. and a pressure between 5 and 100 bar is sufficient for the pre-treatment. The pre-treatment ends when the pressure progressively starts decreasing, which is a signal for formation of substantial amounts of methanol. Surprisingly, the present pre-treatment consumes very little carbon monoxide and hydrogen but yet results in the formation of a catalytic system having a considerably enhanced activity for the production of methanol. At the end of the pre-treatment the temperature may be adjusted to the required reaction temperature, which is a value at which substantial amounts of methanol are produced. This adjustment may be an increase of the temperature, but it is also possible that the temperature can be decreased. Such an increase or decrease of the temperature will usually be over a range of 10° C. to 50° C. It is, however, possible, that no adjustment of the temperature is required at all, pre-treatment and methanol production being carried out at substantially the same temperature.

The process according to the present invention may be carried out at a temperature and a pressure which are not critical and may vary within wide ranges. Preferably, a temperature in the range of from 30° C. to 150° C. and a pressure in the range of from 5 to 100 bar are used.

The process according to the present invention may be carried out with an organic diluent in which the catalytic system is present, at least partly, as a suspension. Suitably, a weight ratio of organic diluent to component (a) in the range of from 0.1 to 5000 is used, but this weight ratio may be lower than 0.1 or higher than 5000. The process according to the present invention is preferably carried out using a molar ratio of component (c) to component (a) in the range of from 0.5:1 to 100:1 and, more preferably, from 1:1 to 50:1, but the use of molar ratio below 0.5 and above 100 is not excluded. The process may be carried out using a molar ratio of component (b) to component (a) which is not critical and may vary within wide ranges, preferably in the range of from 0.1 to 1 to 100 to 1.

Any inert diluent may in principle be used. Examples of suitable diluents are ketones, such as acetone, methyl ethyl ketone, methyl isobutyl ketone, acetophenone, cyclohexanone and acetylacetone; ethers such as anisole, 2,5,8-trioxanonane (also referred to as "diglyme"), diethyl ether, diphenyl ether, diisopropyl ether and tetrahydrofuran; aromatic hydrocarbons, such as benzene, toluene, the three xylenes and ethylbenzene; halogenated aromatic compounds, such as chlorobenzene and o-dichlorobenzen; halogenated alkanes, such as dichloromethane and carbon tetrachloride; alkanes, such as hexane, heptane, octane, 2,2,3-trimethylpentane and kerosene fractions; cycloalkanes, such as cyclohexane and methylcyclohexane; nitriles, such as benzonitrile and acetonitrile; sulfoxides, such as dimethyl sulfoxide; sulfones, such as diisopropyl sulfone; tetrahydrothiophene-1,1-dioxide (also referred to as "sulfolane"), 2-methyl-4-butylsulfolane and 3-methylsulfolane. Mixtures of two or more solvents may be used. Very good results have been obtained with ethers.

The carbon monoxide and hydrogen may be used as pure gases or diluted with an inert gas such as a noble gas or nitrogen. The process according to the present invention may be carried out using a molar ratio carbon monoxide to hydrogen in the gaseous mixture which is not critical and may vary within wide ranges, suitably in the range of from 1:0.2 to 1:20. The carbon monoxide and hydrogen may be obtained by partial oxidation of hydrocarbons, for example, of natural gas. The methanol produced according to the invention may be used for a variety of purposes, for example, for the manufacture of synthetic gasoline, as a fuel component and for the production of methyl tert-butyl ether.

The process according to the present invention may be carried out batchwise, semi-continuously or continuously.

The invention also provides a novel composition prepared by combining the following components:
component (a): a nickel salt of an acid having a $pK_a$, measured in aqueous solution at 25° C., of less than 4.70,
component (b): an alcohol, and
component (c): a hydride of an alkali metal and/or a hydride of an alkaline earth metal.

Said novel composition may be used as a catalytic system in the process according to the present invention.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same results are intended to be within the scope of the instant invention as defined by the instant specification and claims.

The invention is further illustrated by means of the following Examples. Each experiment was carried out in a 300 ml Hastelloy C autoclave ("Hastelloy" is a trade mark) provided with a magnetic stirrer. The sodium hydride was used as a suspension in white paraffin oil containing 80% by weight of NaH. The reaction mixtures were analysed by means of gas-liquid chromatography.

Comparative Experiment A

The autolcave was charged under a nitrogen atmosphere with diglyme (40 ml), nickel acetate.4H$_2$O (10 mmol), sodium hydride (60 mmol) and tert-butyl alcohol (20 mmol), heated to a temperature of 45° C. with stirring and kept at this temperature for 2 hours. Then, a solution of tert-butyl alcohol (30 mmol) in diglyme (50 ml) was introduced into the autoclave, the autoclave was sealed and a mixture of 1 volume of carbon monoxide and 2 volumes of hydrogen was admitted until a pressure of 45 bar was obtained.

The autoclave was further heated to a temperature of 100° C. and the pressure was then kept at a value between 30 and 60 bar by introducing intermittently said mixture of carbon monoxide and hydrogen.

The pressure remained constant after 2 hours at 100° C. which indicates that the catalyst had lost its activity. At this moment the autoclave was allowed to adopt ambient temperature and then depressurized. The reaction mixture contained a black-green solid substance and 2.8 g of methanol and 0.3 g of methyl formate.

EXAMPLE 1

Comparative Experiment A was repeated with the difference that nickel acetate.4H$_2$O (10 mmol) was replaced with nickel format. 2H$_2$O (10 mmol) and that the temperature was kept at 100° C. for 5 hours instead of 2 hours.

At the end of this period of 5 hours the pressure was decreasing which indicates that the catalytic system had retained activity. The reaction mixture contained a yellow solid substance and 3.8 g of methanol; the presence of methyl formate could not be detected.

Comparison of Example 1 with Comparative Experiment A shows that in Example 1 where nickel formate was used more methanol and no methyl formate was formed and that the catalytic system had a longer life.

EXAMPLE 2

The autoclave was charged under a nitrogen atmosphere with diglyme (50 ml), nickel formate.2H$_2$O (10 mmol), sodium hydride (60 mmol) and tert-butyl alcohol (20 mmol), heated to a temperature of 45° C. with stirring and kept at this temperature for 0.5 hour. Then, a solution of tert-butyl alcohol (30 mmol) in diglyme (50 ml) was introduced into the autoclave, the autoclave was sealed and a mixture of 1 volume of carbon monoxide and two volumes of hydrogen was admitted until a pressure of 45 bar was obtained.

The autoclave was further heated to a temperature of 85° C. and kept at this temperature for 2 hours in order to pre-treat the catalytic system. The pressure remained almost constant during these 2 hours which indicated that almost no reaction took place.

The autoclave was further heated to a temperature of 100° C. and the pressure was then kept at a value between 30 and 60 bar by introducing intermittently said mixture of carbon monoxide and hydrogen.

The pressure was still decreasing after 3 hours at 100° C. which indicates that the catalytic system had retained activity. At this moment the autoclave was allowed to adopt ambient temperature and then depressurized. The reaction mixture contained a yellow solid substance, 13.5 g of methanol and 1.5 g of methyl formate.

Comparison of Example 2 where the catalyst had been pre-treated for 2 hours at 85° C. with Example 1 where no pre-treatment had taken place shows that the pre-treatment considerably enhanced the production of methanol.

Comparative Experiment B

Example 2 was repeated with the difference that nickel formate.2H$_2$O (10 mmol) was replaced with nickel acetate.4H$_2$O (10 mmol) and that the reaction was terminated after 4 hours at 100° C. instead of 3 hours at 100° C.

The pressure decreased during the period of 2 hours heating at 85° C. which indicates that pre-treatment of the catalyst and/or methanol formation took place.

At the moment of termination of the experiment the pressure had obtained a constant value which indicates that the catalyst had lost its activity. The reaction mixture contained 3.6 g of methanol and 0.4 g of methyl formate.

Comparison of Comparative Experiment B where nickel acetate was used with Example 2 where nickel formate was used shows that heating for 2 hours at 85° C. in the presence of nickel acetate does not enhance the production of methanol.

EXAMPLE 3

The autoclave was charged under a nitrogen atmosphere with diglyme (50 ml), nickel oxalate.2H$_2$O (10 mmol), sodium hydride (60 mmol) and tert-butyl alcohol (20 mmol), heated to a temperature of 45° C. with stirring and kept at this temperature for 0.5 hour. Then, a solution of tert-butyl alcohol (30 mmol) in diglyme (50 ml) was introduced into the autoclave, the autoclave was sealed and a mixture of 1 volume of carbon monoxide and 2 volumes of hydrogen was admitted until a pressure of 45 bar was obtained.

The autoclave was further heated to a temperature of 100° C. and kept at this temperature for 2 hours in order to pre-treat the catalytic system. The pressure remained almost constant during these 2 hour which indicates that almost no reaction took place.

The autoclave was further heated to a temperature of 120° C. and the pressure was then kept at a value between 30 and 60 bar by introducing intermittently said mixture of carbon monoxide and hydrogen.

The pressure was still decreasing after 2.5 hours at 120° C. which indicates that the catalytic system had retained activity. At this moment the autoclave was allowed to adopt ambient temperature and then depressurized. The reaction mixture contained a yellow solid substance and 6 g of methanol.

Comparative Experiments C and D

Comparative Experiment A was repeated with the difference that nickel acetate.4H$_2$O (10 mmol) was replaced with nickel acetylacetonate (10 mmol, Comparative Experiment C) or nickel cyanide (10 mmol, Comparative Experiment D).

In both cases, the reaction mixture contained a black-green solid substance and no methanol.

Comparative Experiment E

The autoclave was charged under a nitrogen atmosphere with diglyme (100 ml), nickel acetate4.H$_2$O (10 mmol) and potassium tert-butoxide (60 mmol), sealed and pressurized with a mixture of 1 volume of carbon monoxide and 2 volumes of hydrogen until a partial pressure of hydrogen of 30 bar and of carbon monoxide of 15 bar was obtained. The autoclave was heated to a temperature of 80° C., kept at this temperature for 2 hours, then further heated to a temperature of 100° C. and kept at this temperature for 3 hours. At the end of this period the autoclave was allowed to adopt ambient temperature and depressurized.

The reaction mixture contained a black-green solid substance and 0.2 g of methyl formate and less than 0.1 g of methanol.

What is claimed is:

1. A process for the production of methanol which comprises the step of contacting a gaseous mixture comprising carbon monoxide and hydrogen with a catalytic system prepared by combining the following components:
   component (a): a nickel salt of a carboxylic acid having a pK$_a$, measured in aqueous solution at 25° C., of less than 4.70,
   component (b) an alcohol; and
   component (c) a hydride of an alkali metal and/or a hydride of an alkaline earth metal.

2. The process as claimed in claim 1, wherein said salt in component (a) is nickel formate.

3. The process as claimed in claim 1, wherein said salt in component (a) is nickel oxalate.

4. The process as claimed in claim 1, wherein said component (b) is an alkanol.

5. The process as claimed in claim 4, wherein said alkanol has in the range of from 4 to 12 carbon atoms per molecule.

6. The process as claimed in claim 5, wherein said alkanol is tert-butyl alcohol or tert-phenyl alcohol.

7. The process as claimed in claim 1, wherein said component (c) is sodium hydride.

8. The process as claimed in claim 1, wherein said catalytic system is pre-treated by contacting it for a prolonged time with a gaseous mixture comprising carbon monoxide and hydrogen at such an elevated temperature and elevated pressure that no substantial consumption of carbon monoxide and hydrogen takes place.

9. The process as claimed in claim 1, wherein a temperature in the range of from 30° C. to 150° C. and a pressure in the range of from 5 to 100 bar are used.

10. The process as claimed in claim 1, wherein said component (c) is added as a suspension in a mineral oil.

11. The process as claimed in claim 1, wherein said catalyst system further comprises an alcoholate of an alkali metal or an alcoholate of an alkaline earth metal.

12. A process for the production of methanol which comprises the steps of contacting a gasous mixture comprising carbon monoxide and hydrogen with a catalytic system prepared by combining:

(a) a nickel salt selected from the group consisting of nickel formate, nickel oxalate, or a mixture thereof;
(b) an alcohol having from 4 to 12 carbon atoms; and
(c) sodium hydride suspended in a mineral oil; wherein said catalytic system is pretreated by contacting with a gaseous mixture comprising carbon monoxide and hydrogen for a period of time ranging from about ten minutes to about 6 hours at an elevated temperature and an elevated pressure at which no substantial consumption of carbon monoxide and hydrogen takes place; wherein said process for the production of methanol is carried out at a temperature from about 30° C. to about 150°0 C. and a pressure from about 5 to about 100 bar.

* * * * *